United States Patent
Ueno

(10) Patent No.: US 10,772,555 B2
(45) Date of Patent: Sep. 15, 2020

(54) INSOMNIA TREATMENT ASSISTANCE DEVICE AND INSOMNIA TREATMENT ASSISTANCE PROGRAM

(71) Applicant: Sustainable Medicine, Inc., Tokyo (JP)

(72) Inventor: Taro Ueno, Tokyo (JP)

(73) Assignee: SUSTAINABLE MEDICINE, INC., Tokyo (JP)

( * ) Notice: Subject to any disclaimer, the term of this patent is extended or adjusted under 35 U.S.C. 154(b) by 0 days.

(21) Appl. No.: 16/340,727

(22) PCT Filed: Oct. 11, 2016

(86) PCT No.: PCT/JP2016/080128
§ 371 (c)(1),
(2) Date: Apr. 10, 2019

(87) PCT Pub. No.: WO2018/069968
PCT Pub. Date: Apr. 19, 2018

(65) Prior Publication Data
US 2019/0313964 A1    Oct. 17, 2019

(51) Int. Cl.
*A61B 5/00*    (2006.01)
*A61B 5/16*    (2006.01)
*A61M 21/02*   (2006.01)

(52) U.S. Cl.
CPC ............. *A61B 5/4806* (2013.01); *A61B 5/16* (2013.01); *A61M 21/02* (2013.01)

(58) Field of Classification Search
CPC ... A61B 5/4812; A61B 5/4815; A61B 5/4809; A61B 5/7264; A61B 5/4806; A61B 5/746; A61B 5/165; A61B 5/486
See application file for complete search history.

(56) References Cited

U.S. PATENT DOCUMENTS

| 2006/0019224 A1 | 1/2006 | Behar et al. |
| 2011/0015495 A1* | 1/2011 | Dothie ................. A47C 31/123 600/300 |
| 2016/0020718 A1 | 1/2016 | Tang |

FOREIGN PATENT DOCUMENTS

| CN | 1724086 A | 1/2006 |
| CN | 105899129 A | 8/2016 |

(Continued)

OTHER PUBLICATIONS

Office Action dated Nov. 18, 2019 issued in corresponding Chinese Patent Application No. 201680089968.3 (9 pages).

(Continued)

*Primary Examiner* — Christine H Matthews
*Assistant Examiner* — Joshua Daryl D Lannu
(74) *Attorney, Agent, or Firm* — Polsinelli PC

(57) ABSTRACT

Provided is an insomnia treatment assistance device including: a bedtime setting unit that sets a bedtime of a user on the basis of sleep efficiency of the user and notifies it to the user; an execution time setting unit that sets a time earlier than the bedtime by a first predetermined time as a sleepiness test execution time; and a reminder message presentation unit that presents a reminder message for prompting execution of a sleepiness test to the user at the sleepiness test execution time. The sleepiness test can be performed at an appropriate time depending on the sleep efficiency that suggests a degree of amelioration of insomnia even in a case where the sleepiness test is performed once a day. It is possible to appropriately measure user's sleepiness depending on the degree of amelioration of insomnia while minimizing a user's burden for the sleepiness test.

18 Claims, 3 Drawing Sheets

(56) References Cited

FOREIGN PATENT DOCUMENTS

| | | |
|---|---|---|
| EP | 1 618 913 A1 | 1/2006 |
| JP | 2003-210587 A | 7/2003 |
| JP | 2006-034966 A | 2/2006 |
| JP | 2011-036649 A | 2/2011 |
| JP | 2012-40134 A | 3/2012 |
| JP | 2015-115045 A | 6/2015 |

OTHER PUBLICATIONS

European Search Report dated Sep. 24, 2019 in European Patent Application No. 16918706.9 (7 pages).

* cited by examiner

INSOMNIA TREATMENT ASSISTANCE DEVICE AND INSOMNIA TREATMENT ASSISTANCE PROGRAM

CROSS REFERENCE TO RELATED APPLICATIONS

This application is a National Phase filing under 35 U.S.C. § 371 of PCT/JP2016/080128 filed on Oct. 11, 2016, the entire contents of which are hereby incorporated by reference.

TECHNICAL FIELD

The present invention relates to an insomnia treatment assistance device and an insomnia treatment assistance program for assisting treatment of insomnia.

BACKGROUND ART

Currently, many people suffer from insomnia. The insomnia refers to a symptom including "sleep onset insomnia" such as difficulty in falling asleep in the night, "middle-of-the-night insomnia" such as difficulty in maintaining sleep, "sleep offset insomnia" such as waking up early in the morning. If such a symptom continues, it is difficult to sleep well. Therefore, this causes sleepiness during daytime, distraction of attention, fatigue, or various physical disorders.

In the related art, there is known a system for managing sleep of a user from the viewpoint of improvement of sleep quality of the user (for example, see Patent Document 1). In the system described in Patent Document 1, one or more objective parameters regarding the sleep quality of the user who is in bed are monitored, and a feedback of objective test data measured for a cognitive ability or a psychomotor ability during a wake-up time of the user is presented to the user via a portable device such as a mobile phone.

Patent Document 1 describes a method of measuring a response time as an example of the cognitive ability test or psychomotor ability test (method of measuring accumulated sleepiness, feeling disorders, and degradation of the psychomotor ability caused by insomnia when a user has sleep limited to four to five hours per night, for one week). In the system described in Patent Document 1, in order to improve the future sleep quality on the basis of a result of the cognitive ability test or the like, information for affecting a user's behavior (such as a warning, guidance, advice, or a message for encouraging the user) is presented to the user.

In addition to Patent Document 1, a method of performing the sleepiness test on the basis of the response time is known (for example, see Patent Documents 2 and 3). Patent Document 2 describes a technique of detecting a response from a user to a generated vibration and determining a user's wakening level on the basis of an actual time length during which there is no response from the user. Patent Document 3 describes a technique of designating and notifying a user to select any one of operation switches randomly set using a sound output of a loudspeaker and determining a sleepiness degree of the user from response time information taken until the designated operation switch is operated.

In the system described in Patent Document 1, since information such as a warning, a guide, advice, or a message for encouraging the user is presented on the basis of a result of the test or the like through measurement of the response time of the user, the sleep quality is improved when the user takes actions in accordance with the content.

Note that insomnia is not cured immediately even when the user takes actions once in accordance with the presented information depending on the result of a single test. For this reason, it is necessary to continuously perform the test and continuously take actions for improving insomnia.

Patent Document 1 describes a technique of periodically executing the test while a user is awake on the basis of a fact that the cognitive ability or the psychomotor ability changes throughout the entire day. In addition, Patent Document 1 also describes a technique of randomly or sporadically performing the test while the user is awake. Specifically, the cognitive ability test or the psychomotor ability test is performed several times a day for several days over a wide range of time. The user is prompted by a portable device to execute the test at a regular time everyday for several days.

Patent Document 1: JP-A-2011-36649
Patent Document 2: JP-A-2012-40134
Patent Document 3: JP-A-2015-115045

SUMMARY OF THE INVENTION

In the system described in Patent Document 1, in order to obtain information regarding the cognitive ability or the psychomotor ability at maximum with the minimum number of tests so as not to be a burden to the user, the time for performing the test is defined by a processing unit in advance. However, since the user is necessary to execute a plurality of tests (it is stated that the test is preferably performed every one to eight hours), a burden is large, and there is a high possibility that the treatment may be abandoned without being continuously performed, disadvantageously.

As one of the methods for addressing such a problem, it is conceivable to reduce the number of tests as small as possible. However, as described in Patent Document 1, in the method of executing the test at the same fixed time everyday, there is a problem that it is difficult to appropriately evaluate the user's cognitive ability or psychomotor ability. Although these abilities change throughout a day and also change depending on the degree of amelioration of insomnia, it is difficult to perform the test by taking this fact into consideration.

In order to address such a problem, an object of the present invention is to appropriately measure the user's sleepiness depending on a degree of amelioration of insomnia while minimizing a user's burden for performing the sleepiness test.

In order to address the aforementioned problem, according to the present invention, a user's bedtime is set on the basis of user's sleep efficiency, and a time earlier than the bedtime by a first predetermined time is set as a sleepiness test execution time. In addition, a message for prompting execution of the sleepiness test is presented to the user at the set execution time or at a time earlier or later than the execution time by a second predetermined time.

According to the present invention having the aforementioned configuration, on the basis of the sleep efficiency that suggests the degree of amelioration of insomnia of the user, an appropriate bedtime for amelioration of insomnia is set, and a time earlier than the bedtime by the first predetermined time is set as the sleepiness test execution time. In addition, a message for prompting execution of the sleepiness test is presented to the user at the execution time or a time earlier or later than the execution time by the second predetermined time, so that the user is prompted by this message to perform the sleepiness test. For this reason, the sleepiness test is performed at an appropriate time depending on the degree of amelioration of insomnia even in a case where the sleepiness test is performed only once a day. As a result, it is possible to appropriately measure the user's sleepiness depending on the degree of amelioration of insomnia while minimizing a user's burden for performing the sleepiness test.

MODE FOR CARRYING OUT THE INVENTION

Figure 1:
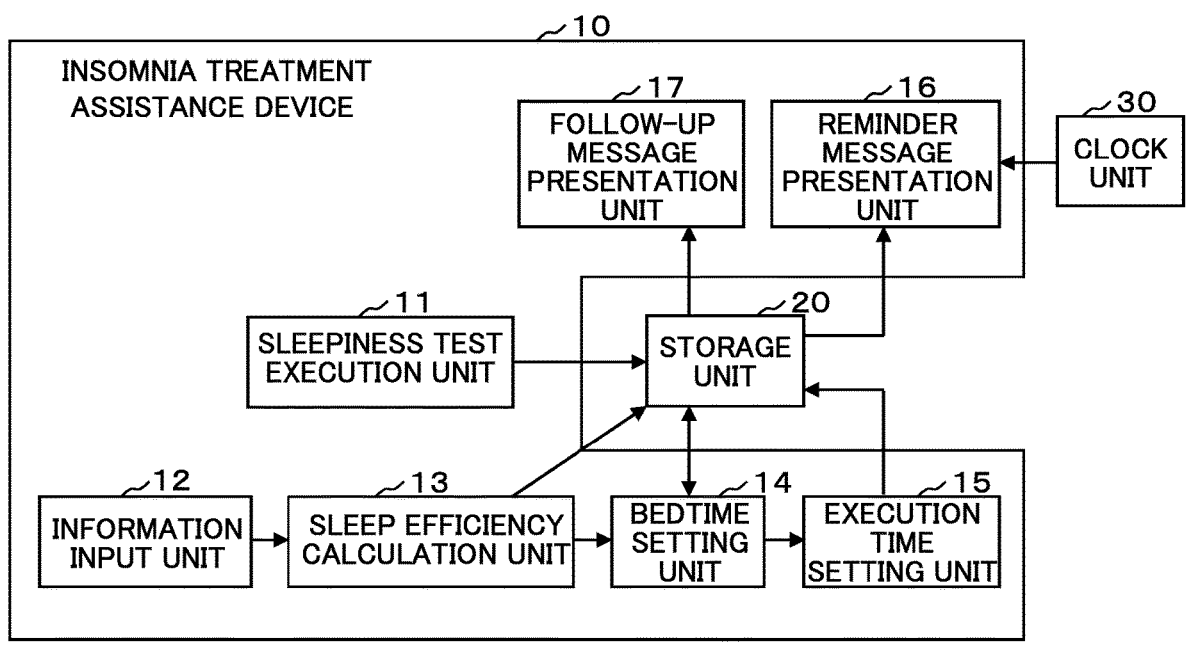
FIG. 1 is a block diagram illustrating a functional configuration example of an insomnia treatment assistance device according to an embodiment of the invention.

An embodiment of the invention will now be described with reference to the accompanying drawings. FIG. 1 is a block diagram illustrating a functional configuration example of an insomnia treatment assistance device according to an embodiment of the invention. An insomnia treatment assistance device 10 according this embodiment is mounted on a portable terminal such as a smart phone or a tablet computer, and its functional configuration includes a sleepiness test execution unit 11, an information input unit 12, a sleep efficiency calculation unit 13, a bedtime setting unit 14, an execution time setting unit 15, an reminder message presentation unit 16, and a follow-up message presentation unit 17. Note that, although it is assumed herein that the insomnia treatment assistance device is mounted on a portable terminal, it may be mounted on a non-portable computer such as a personal computer.

Each of the functional blocks 11 to 17 described above may be configured using any one of hardware, a digital signal processor (DSP), and software. For example, in a case where each of the functional blocks 11 to 17 is configured using software, each of them includes a CPU, a RAM, a ROM, or the like of the portable terminal and is implemented by operating an insomnia treatment assistance program stored in a storage medium such as a RAM, a ROM, a hard disk, or a semiconductor memory in practice. Note that the insomnia treatment assistance program (hereinafter, referred to as "insomnia treatment application") may be downloaded via a network such as the Internet and may be installed in the portable terminal.

As illustrated in FIG. 1, the portable terminal includes a storage unit 20 and a clock unit 30 in addition to the insomnia treatment assistance device 10. The storage unit 20 is a storage medium such as a RAM, a hard disk, or a semiconductor memory. This storage medium may be a storage medium storing the insomnia treatment assistance program or may be other types of storages. The clock unit 30 is a unit for measuring a date/time using a timepiece function.

Each functional configuration of the insomnia treatment assistance device 10 will now be described. The sleepiness test execution unit 11 executes a test for measuring a sleepiness degree of a user during daytime. A person suffering from insomnia has sleepiness during daytime because of insufficient sleep at night in many cases. It is possible to estimate a severity level of insomnia on the basis of the sleepiness degree during daytime. In addition, it is possible to estimate whether the insomnia is being cured or worsened, or how much the insomnia is progressed by repeatedly performing the sleepiness test.

For example, the sleepiness test execution unit 11 measures a time elapsed after performing predetermined display on a display unit of the portable terminal or outputting a predetermined sound from a loudspeaker until a user makes a predetermined response operation, and determines a sleepiness degree (or wakening level) on the basis of the elapse time (response speed). In this case, it is determined that the sleepiness degree is higher as the response time is longer. Specifically, the sleepiness degree can be calculated on the basis of a predetermined function in which the response time is included as a parameter. Alternatively, the sleepiness degree may be determined from the response time on the basis of table information obtained by dividing the sleepiness degree into a plurality of levels and associating the response time with the sleepiness degree.

According to this embodiment, the sleepiness test described above is performed once a day, and the result is stored in the storage unit 20. Note that the content of the sleepiness test is not limited to the aforementioned example, and other methods known in the art may also be applied.

The information input unit 12 inputs information regarding a bedtime, a fall-asleep time, a wakening time, and a get-up time of a user through a user operation on an input interface (such as a touch panel or a keyboard) of the portable terminal. This information input is performed everyday. Note that, since it is difficult for a user to check the accurate fall-asleep time, an approximate time that the user subjectively estimates may be input.

The sleep efficiency calculation unit 13 calculates the user's sleep efficiency on the basis of the information regarding the bedtime, the fall-asleep time, the wakening time, and the get-up time input through the information input unit 12 and stores the result in the storage unit 20. The sleep efficiency refers to a percentage of time during which the user actually sleeps out of a total time during which the user stays in a bunk such as a bed. That is, the sleep efficiency is calculated using the following formula.

Sleep efficiency=(time from fall-asleep time to wakening time)/(time from bedtime to get-up time)×100[%]

The bedtime setting unit 14 sets the user's bedtime on the basis of the sleep efficiency calculated by the sleep efficiency calculation unit 13 and notifies it to the user. This bedtime setting using the bedtime setting unit 14 may be performed everyday or on a predetermined period basis (for example, for a week). For example, in a case where the bedtime setting is performed on a week basis, the bedtime setting unit 14 sets the bedtime on the basis of an average value of the sleep efficiency calculated by the sleep efficiency calculation unit 13 for a week (stored in the storage unit 20) and notifies the bedtime to the user.

According to this embodiment, in a case where the sleep efficiency calculated by the sleep efficiency calculation unit 13 is lower than a predetermined value (for example, 80%), the bedtime setting unit 14 sets a time later than the previous set bedtime by a predetermined time (for example, fifteen minutes) as the next bedtime. Meanwhile, in a case where the sleep efficiency calculated by the sleep efficiency calculation unit 13 is equal to or higher than a predetermined value (for example, 85%), the bedtime setting unit 14 sets a time earlier than the previous set bedtime by a predetermined time (for example, fifteen minutes) as the next bedtime. The bedtime setting unit 14 stores the previous set bedtime and the current set bedtime in the storage unit 20 and manages them.

Note that, although the predetermined value (80%) used as a threshold value in the case of setting the bedtime later than the previous one is different from the predetermined value (85%) used as a threshold value in the case of setting the bedtime earlier than the previous one, they may be set as the same value. In addition, as a condition for the case of setting the bedtime earlier than the previous one, a result of the sleepiness test using the sleepiness test execution unit 11 may be used in addition to the value of the sleep efficiency. For example, in a case where the sleep efficiency calculated by the sleep efficiency calculation unit 13 is equal to or higher than a predetermined value (for example, 85%), and the sleepiness degree measured by the sleepiness test is improved relative to the previous one, a time earlier than the previous set bedtime is set as the next bedtime.

The bedtime setting unit 14 notifies the bedtime set as described above to a user through display on the display unit of the portable terminal or the like. The user strives to go to bed at the notified bedtime. By repeating this everyday, it is possible to anticipate improvement of insomnia.

Many people suffering from insomnia of difficulty in falling asleep feel uneasy in being unable to sleep soon even after going to bed, and such a sense of uneasiness itself also disturbs sleep. Such a person tends to go to bed at an early time even not in a sleepy state due to the sense of uneasiness in being unable to sleep immediately. This also has the negative effect, so that a period of time from the bedtime to the fall-asleep time (the time in bed without sleeping) becomes longer, and the sleep efficiency is degraded. In this regard, by forcibly delaying the bedtime, a user may be given a sense of easiness that the user is not necessary to forcefully go to bed at an early time. In addition, since the user goes to bed when becoming sleepy to some extent, it can be expected that the period of time from the bedtime to the fall-asleep time can be shortened.

The execution time setting unit 15 sets, as a sleepiness test execution time, a time earlier than the bedtime set by the bedtime setting unit 14 by a first predetermined time (for example, three hours earlier) and stores it in the storage unit 20. When the date/time measured by the clock unit 30 reaches the sleepiness test execution time stored in the storage unit 20, the reminder message presentation unit 16 presents a message for prompting execution of the sleepiness test to the user. For example, at the sleepiness test execution time, the reminder message presentation unit 16 notifies a reminder message to the display unit of the portable terminal in a pushing manner. In this case, an alarm sound may be output from a loudspeaker of the portable terminal.

Note that, although the reminder message is notified at the sleepiness test execution time set by the execution time setting unit 15 in this example, it may not be the execution time itself. For example, the reminder message may be notified at a time earlier or later than the sleepiness test execution time set by the execution time setting unit 15 by a second predetermined time. The user receives this reminder message and executes the sleepiness test using the sleepiness test execution unit 11.

As described above, the timing at which the reminder message is notified to the user is a time earlier than the bedtime set by the bedtime setting unit 14 by the first predetermined time. Here, the bedtime set by the bedtime setting unit 14 is a time appropriately set depending on the insomnia state at that time on the basis of the result of the sleepiness test. Therefore, it is possible to perform the sleepiness test at an appropriate time depending on the degree of amelioration of insomnia when the user receives the reminder message and executes the sleepiness test. In addition, the bedtime setting unit 14 re-establishes the bedtime as necessary on the basis of the execution result of the sleepiness test performed at the appropriate time. By repeating this process, treatment of insomnia can proceed.

The follow-up message presentation unit 17 presents a follow-up message for affecting a user's behavior to the user depending on the bedtime set by the bedtime setting unit 14. For example, the follow-up message presentation unit 17 displays the follow-up message on the display unit of the portable terminal when the bedtime setting unit 14 sets the bedtime. Note that the timing for presenting the follow-up message is not limited to the time at which the bedtime is set. For example, the follow-up message may be presented simultaneously when the reminder message is presented.

Specifically, in a case where the bedtime setting unit 14 sets a time later than the previous set bedtime as the next bedtime, the follow-up message presentation unit 17 presents a follow-up message for correcting or guiding the user's behavior. In many cases, during the first half of the treatment, the bedtime is set to the time later than the previous one. For this reason, in this case, it would be meaningful to present a follow-up message such as "since sleep efficiency is still low, it is recommended not to go to bed until the scheduled bedtime." to the user.

Meanwhile, in a case where the bedtime setting unit 14 sets a time earlier than the previous one as the next bedtime, the follow-up message presentation unit 17 presents a follow-up message for supporting the user's behavior. In many cases, during the second half of the treatment, the bedtime is set to a time earlier than the previous one. For this reason, in this case, it would be meaningful to present a follow-up message such as "Treatment has been progressed successfully, and sleep efficiency has been improved. Sleepiness during daytime will be gradually treated if you continuously maintain this condition." to the user.

Figure 2:
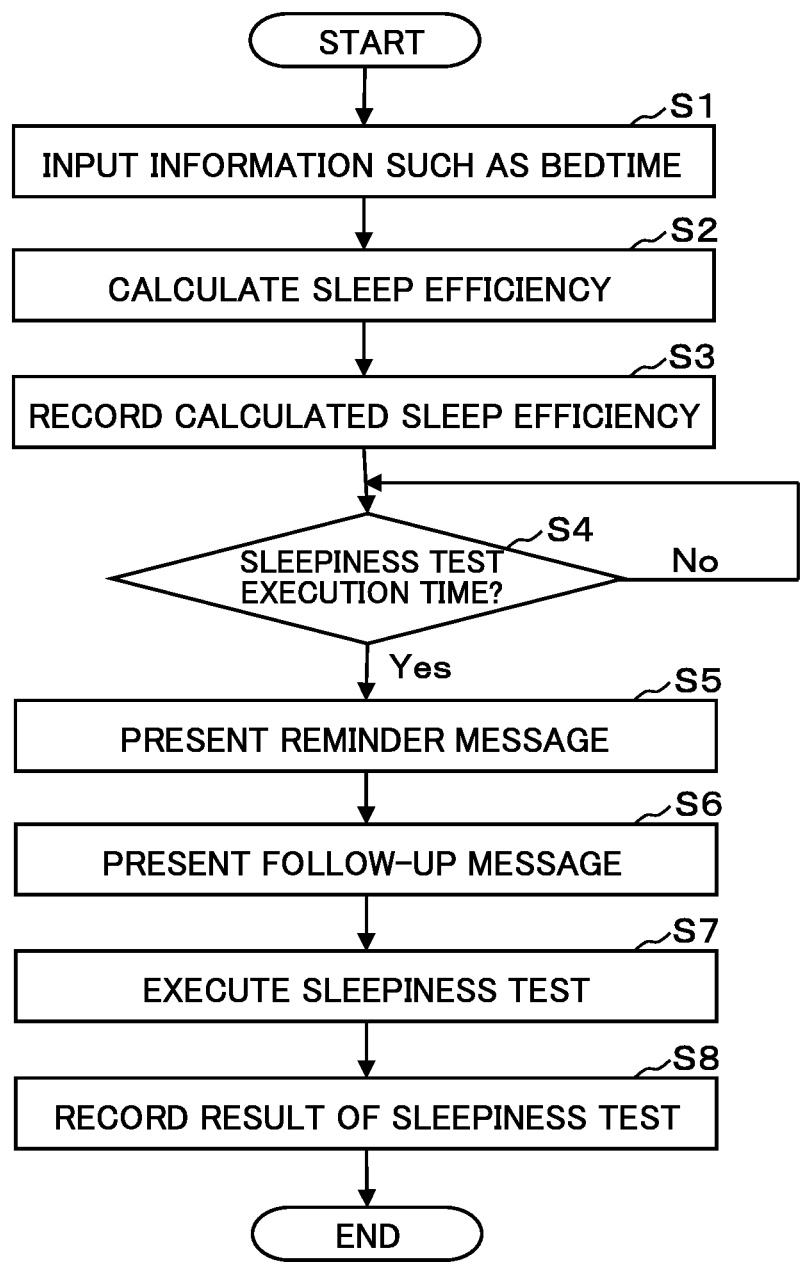
FIG. 2 is a flowchart illustrating an operation example of the insomnia treatment assistance device according to an embodiment of the invention.
Figure 3:
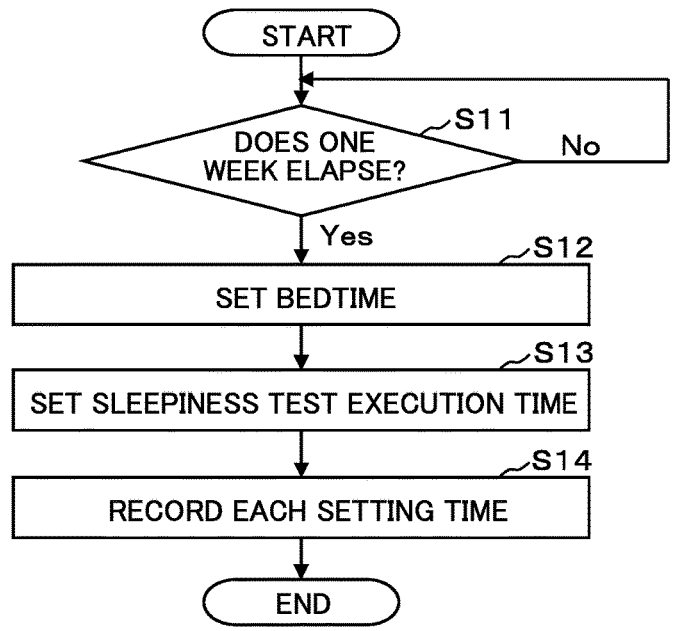
FIG. 3 is a flowchart illustrating an operation example of the insomnia treatment assistance device according to an embodiment of the invention.

FIGS. 2 and 3 are flowcharts illustrating an operation example of the insomnia treatment assistance device 10 according to this embodiment configured as described above. The flowchart of FIG. 2 illustrates an operation example executed by the insomnia treatment application on a daily basis. In addition, the flowchart of FIG. 3 illustrates an operation example executed on a predetermined period basis (for example, for one week).

First, the flowchart of FIG. 2 will be described. The information input unit 12 inputs information regarding a bedtime, a fall-asleep time, a wakening time, and a get-up time of a user through a user operation on the input interface of the portable terminal (step S1). This information input is performed when the user gets-up every morning. That is, the information input unit 12 inputs the bedtime and the fall-asleep time of the last night and the wakening time and the get-up time of today morning.

Next, the sleep efficiency calculation unit 13 calculates the user's sleep efficiency on the basis of the information regarding the bedtime, the fall-asleep time, the wakening time, and the get-up time input by the information input unit 12 (step S2). In addition, the sleep efficiency calculation unit 13 stores the information regarding the calculated sleep efficiency in the storage unit 20 (step S3).

Then, the reminder message presentation unit 16 determines whether or not the sleepiness test execution time has come (step S4). Note that this sleepiness test execution time is set by the execution time setting unit 15 in the flowchart of FIG. 3. Here, in a case where the sleepiness test execution time has not yet come, the determination of step S4 is repeatedly executed.

Meanwhile, when it is determined that the sleepiness test execution time has come, the reminder message presentation unit 16 prompts the user to perform the sleepiness test by displaying a reminder message on the display unit of the portable terminal (step S5). In addition, the follow-up message presentation unit 17 displays a follow-up message for affecting a user's behavior on the display unit of the portable terminal (step S6). The content of the follow-up message to be displayed at this time is determined depending on the bedtime set by the bedtime setting unit 14 in the flowchart of FIG. 3.

Then, the sleepiness test execution unit 11 executes the sleepiness test through a user operation on the input interface of the portable terminal (step S7). In addition, the sleepiness test execution unit 11 stores information representing the user's daytime sleepiness degree measured through the sleepiness test in the storage unit 20 (step S8). As a result, the daily processing illustrated in the flowchart of FIG. 2 is terminated. The operation of FIG. 2 is repeatedly executed on a daily basis.

Then, the flowchart of FIG. 3 will be described. The bedtime setting unit 14 determines whether or not a week has elapsed from the previous bedtime setting (step S11). Here, in a case where a week has not yet elapsed, the determination of step S11 is repeatedly executed.

Meanwhile, in a case where a week has elapsed from the previous bedtime setting, the bedtime setting unit 14 sets the user's bedtime on the basis of the sleep efficiency calculated by the sleep efficiency calculation unit 13 (a weekly average of the sleep efficiency values stored in the storage unit 20) and notifies the user's bedtime to the user (step S12). Note that the bedtime initially input by the information input unit 12 is directly set immediately after the insomnia treatment application starts to be used.

Then, the execution time setting unit 15 sets a time earlier than the bedtime set by the bedtime setting unit 14 by a first predetermined time (for example, three hours earlier) as the sleepiness test execution time (step S13). In addition, the bedtime setting unit 14 and the execution time setting unit 15 store the bedtime and the sleepiness test execution time set as described above in the storage unit 20 (step S14). As a result, the processing of the flowchart of FIG. 3 is terminated.

As described above in detail, according to this embodiment, the bedtime setting unit 14 sets the user's bedtime on the basis of the user's sleep efficiency calculated by the sleep efficiency calculation unit 13, and the execution time setting unit 15 sets a time earlier than this bedtime by a first predetermined time as the sleepiness test execution time. In addition, the reminder message presentation unit 16 presents a message for prompting execution of the sleepiness test to the user at the set execution time or at a time earlier or later than the set execution time by a second predetermined time.

According to this embodiment configured as described above, an appropriate bedtime for improving insomnia is set on the basis of the sleep efficiency that suggests a degree of amelioration of the user's insomnia, and a time earlier than this bedtime by a first predetermined time is set as the sleepiness test execution time. In addition, a message for prompting execution of the sleepiness test is presented to the user at this execution time or at the time earlier or later than the execution time by a second predetermined time, and the user is prompted by this message to perform the sleepiness test. For this reason, the sleepiness test is performed at an appropriate time depending on the degree of amelioration of insomnia even in a case where the sleepiness test is performed once a day. As a result, it is possible to appropriately measure the user's sleepiness depending on the degree of amelioration of insomnia while minimizing a user's burden for performing the sleepiness test.

According to this embodiment, the follow-up message presentation unit 17 presents a follow-up message for affecting a user's behavior to the user depending on the bedtime set by the bedtime setting unit 14. As a result, since an appropriate follow-up message depending on the degree of amelioration of insomnia is presented to the user, it is possible to promote a user's motivation for continuously performing the treatment.

Figure 4:
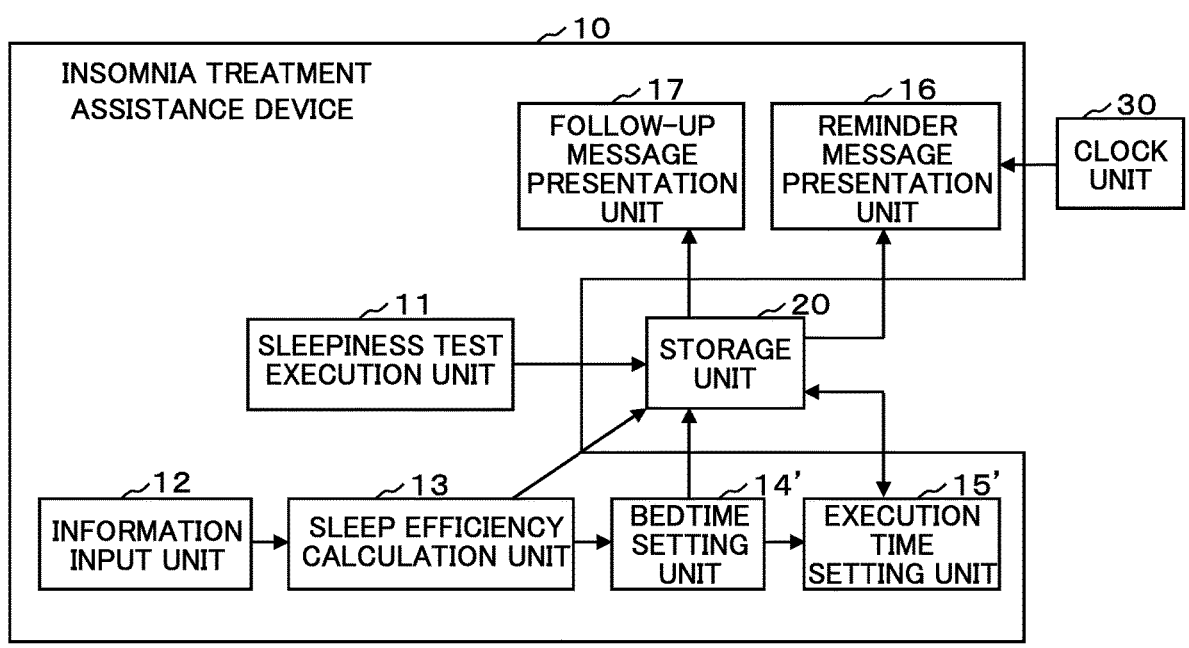
FIG. 4 is a block diagram illustrating another functional configuration example of the insomnia treatment assistance device according to an embodiment of the invention.

Note that, although an example has been described in the aforementioned embodiment, in which the user's bedtime is set on the basis of the sleep efficiency calculated by the sleep efficiency calculation unit 13, and a time earlier than this bedtime by a first predetermined time is set as the sleepiness test execution time, the present invention is not limited thereto. For example, as illustrated in FIG. 4, the sleepiness test execution time may be set on the basis of the sleep efficiency calculated by the sleep efficiency calculation unit 13, and a time later than this execution time by a first predetermined time may be set as the user's bedtime. That is, in the configuration of FIG. 4, an execution time setting unit 15' sets the sleepiness test execution time on the basis of the sleep efficiency calculated by the sleep efficiency calculation unit 13. In addition, a bedtime setting unit 14' sets a time later than the sleepiness test execution time set by the execution time setting unit 15' by a first predetermined time as the user's bedtime.

Although an example has been described in the aforementioned embodiment, in which the information input unit 12 inputs the information regarding the bedtime, the fall-asleep time, the wakening time, and the get-up time through a user operation on the portable terminal, the present invention is not limited thereto. For example, a sensor for detecting transition to a falling asleep state of a user or a sensor for detecting transition to a wakened state may be provided, so that a time at which the transition is detected by such a sensor may be input by the information input unit 12. Note that a sensor known in the art, such as a sensor for detecting user's breathing, a sensor for detecting an angular velocity at a user's chest or abdomen, or a sensor for detecting a brain wave, may be employed as the sensor for this case.

In the aforementioned embodiment, it is desirable that a user who is anxious about insomnia receives prescription from a doctor through a medical interview or the like, installs the insomnia treatment assistance application in accordance with the prescription, and inputs the bedtime as an initial setting.

Any one of the aforementioned embodiments merely shows an example for embodying the present invention, and is not construed as a limitation of the technical scope of the present invention. That is, various forms may be possible without departing from the spirit and scope of the invention.

REFERENCE SIGNS LIST

10 Insomnia treatment assistance device
11 Sleepiness test execution unit
12 Information input unit
13 Sleep efficiency calculation unit
14, 14' Bedtime setting unit
15, 15' Execution time setting unit 16 Reminder message presentation unit
17 Follow-up message presentation unit

The invention claimed is:
1. An insomnia treatment assistance device comprising:
a non-transitory computer readable medium storing instructions;
a processor programed to cooperate with the instructions to perform operations including:
calculating sleep efficiency of a user based on information regarding a prior bedtime, a prior fall-asleep time, a prior wakening time, and a prior get-up time of the user;
setting a first sleepiness test execution time of the insomnia treatment assistance device earlier than the prior bedtime by a first predetermined time, the first predetermined time being based on the calculated sleep efficiency; and
displaying on a terminal of the insomnia treatment assistance device a content prompting execution of a sleepiness test in response to:
the first sleepiness test execution time; or
a time earlier or later than the first sleepiness test execution time by a second predetermined time.

2. The insomnia treatment assistance device according to claim 1, the operations further comprising:
running the calculating, setting and displaying for a predetermined number of cycles;
determining, in response to completion of the running, a next bedtime based on the calculated sleep efficiency during at least some of the predetermined number of cycles;
setting a second sleepiness test execution time earlier than the next bedtime by a third predetermined time, the third predetermined time being based on the calculated sleep efficiency during at least some of the predetermined number of cycles; and
displaying a content prompting execution of the sleepiness test in response to:
a second sleepiness test execution time; or
a time earlier or later than the second sleepiness test execution time by a fourth predetermined time.

3. The insomnia treatment assistance device according to claim 2, wherein:
the determining determines that the next bedtime is later than the prior bedtime in response to at least the sleep efficiency being lower than a predetermined value; and
the determining determines that the next bedtime is earlier than the prior bedtime in response to at least the sleep efficiency being greater than a predetermined value.

4. The insomnia treatment assistance device according to claim 3, the operations further comprising:
displaying a follow-up message of a content of affecting a behavior of the user, the content being based on whether the next bedtime is earlier than or later than the prior bedtime.

5. The insomnia treatment assistance device according to claim 4, the content of the follow-up message comprising:
in response to the next bedtime being later than the prior bedtime, instructions for modifying user behavior to improve sleep efficiency.

6. The insomnia treatment assistance device according to claim 4, the content of the follow-up message comprising:
in response to the next bedtime being earlier than the prior bedtime, support for user behavior.

7. An insomnia treatment assistance method for an insomnia treatment assistance device, the method comprising:

calculating sleep efficiency of a user based on information regarding a prior bedtime, a prior fall-asleep time, a prior wakening time, and a prior get-up time of the user;
setting a first sleepiness test execution time of the insomnia treatment assistance device earlier than the prior bedtime by a first predetermined time, the first predetermined time being based on the calculated sleep efficiency; and
displaying on a terminal of the insomnia treatment assistance device a content prompting execution of a sleepiness test in response to:
the first sleepiness test execution time; or
a time earlier or later than the first sleepiness test execution time by a second predetermined time.

8. The insomnia treatment assistance method according to claim 7, further comprising:
running the calculating, setting and displaying for a predetermined number of cycles;
determining, in response to completion of the running, a next bedtime based on the calculated sleep efficiency during at least some of the predetermined number of cycles;
setting a second sleepiness test execution time earlier than the next bedtime by a third predetermined time, the third predetermined time being based on the calculated sleep efficiency during at least some of the predetermined number of cycles; and
displaying a content prompting execution of the sleepiness test in response to:
a second sleepiness test execution time; or
a time earlier or later than the second sleepiness test execution time by a fourth predetermined time.

9. The insomnia treatment assistance method according to claim 8, wherein:
the determining determines that the next bedtime is later than the prior bedtime in response to at least the sleep efficiency being lower than a predetermined value; and
the determining determines that the next bedtime is earlier than the prior bedtime in response to at least the sleep efficiency being greater than a predetermined value.

10. The insomnia treatment assistance method according to claim 9, further comprising:
displaying a follow-up message of a content of affecting a behavior of the user, the content being based on whether the next bedtime is earlier than or later than the prior bedtime.

11. The insomnia treatment assistance method according to claim 10, the content of the follow-up message comprises:
in response to the next bedtime being later than the prior bedtime, instructions for modifying user behavior to improve sleep efficiency.

12. The insomnia treatment assistance method according to claim 10, the content of the follow-up message comprises:
in response to the next bedtime being earlier than the prior bedtime, support for user behavior.

13. A non-transitory computer readable medium storing instructions which when executed by a processor perform operations comprising:
calculating sleep efficiency of a user based on information regarding a prior bedtime, a prior fall-asleep time, a prior wakening time, and a prior get-up time of the user;
setting a first sleepiness test execution time of an insomnia treatment assistance device earlier than the prior bedtime by a first predetermined time, the first predetermined time being based on the calculated sleep efficiency; and displaying on a terminal of the insomnia treatment assistance device a content prompting execution of a sleepiness test in response to:

the first sleepiness test execution time; or a time earlier or later than the first sleepiness test execution time by a second predetermined time.

14. The non-transitory computer readable medium according to claim 13, the operations further comprising:

running the calculating, setting and displaying for a predetermined number of cycles;

determining, in response to completion of the running, a next bedtime based on the calculated sleep efficiency during at least some of the predetermined number of cycles;

setting a second sleepiness test execution time earlier than the next bedtime by a third predetermined time, the third predetermined time being based on the calculated sleep efficiency during at least some of the predetermined number of cycles; and displaying a content prompting execution of the sleepiness test in response to:

a second sleepiness test execution time; or a time earlier or later than the second sleepiness test execution time by a fourth predetermined time.

15. The non-transitory computer readable medium according to claim 14, wherein:

the determining determines that the next bedtime is later than the prior bedtime in response to at least the sleep efficiency being lower than a predetermined value; and the determining determines that the next bedtime is earlier than the prior bedtime in response to at least the sleep efficiency being greater than a predetermined value.

16. The non-transitory computer readable medium according to claim 15, the operations further comprising:

displaying a follow-up message of a content of affecting a behavior of the user, the content being based on whether the next bedtime is earlier than or later than the prior bedtime.

17. The non-transitory computer readable medium according to claim 16, the content of the follow-up message comprises:

in response to the next bedtime being later than the prior bedtime, instructions for modifying user behavior to improve sleep efficiency.

18. The non-transitory computer readable medium according to claim 16, the content of the follow-up message comprises:

in response to the next bedtime being earlier than the prior bedtime, support for user behavior.

* * * * *